(12) United States Patent
Hirsch et al.

(10) Patent No.: US 7,695,279 B2
(45) Date of Patent: Apr. 13, 2010

(54) DRILL STOP SLEEVE FOR A DENTAL DRILL, DENTAL DRILL DEVICE WITH A DRILL STOP SLEEVE, AND SET CONTAINING SEVERAL DRILL STOP SLEEVES

(75) Inventors: Erika Hirsch, Füllinsdorf (CH); Patrick Näf, Zürich (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 11/754,491

(22) Filed: May 29, 2007

(65) Prior Publication Data
US 2007/0298375 A1    Dec. 27, 2007

(30) Foreign Application Priority Data
Jun. 16, 2006    (EP)    ................. 06 0 12358

(51) Int. Cl.
*A61B 17/16*    (2006.01)
(52) U.S. Cl. ......................................... 433/75; 408/202
(58) Field of Classification Search .................. 433/72,
433/75, 76, 165; 606/80, 172; 408/202,
408/241 S
See application file for complete search history.

(56) References Cited

U.S. PATENT DOCUMENTS

| 74,466 | A |   | 2/1868 | Whiting |  |
|---|---|---|---|---|---|
| 2,700,905 | A |   | 2/1955 | Urquhart |  |
| 4,993,894 | A |   | 2/1991 | Fischer |  |
| 5,078,552 | A | * | 1/1992 | Albel | ........................ 408/1 R |
| 5,078,605 | A |   | 1/1992 | Sutter |  |
| 5,429,504 | A | * | 7/1995 | Peltier et al. | ................. 433/165 |
| 5,788,488 | A |   | 8/1998 | Grossman |  |
| 5,941,706 | A | * | 8/1999 | Ura | ........................... 433/165 |
| 6,514,258 | B1 |   | 2/2003 | Brown |  |
| 6,739,872 | B1 |   | 5/2004 | Turri |  |
| 7,258,513 | B2 | * | 8/2007 | Gertner | ....................... 408/67 |
| 2005/0106531 | A1 |   | 5/2005 | Tang |  |

(Continued)

FOREIGN PATENT DOCUMENTS

DE    9106606 U1    9/1992

(Continued)

OTHER PUBLICATIONS

Search Reports from the European Patent Office (dated Dec. 14, 2006 and Mar. 9, 2007) in corresponding application EP 06 01 2358.

*Primary Examiner*—Ralph A Lewis
(74) *Attorney, Agent, or Firm*—Rissman, Hendricks & Oliverio, LLP

(57) ABSTRACT

A dental drill (10) defining a bore diameter and a drill stop sleeve (22) which is transparent or translucent, thereby improving the view of the drilled hole formed by the drilling during the operation. The drill stop sleeve (22) comprises an uninterrupted circumferential lip (34), which interacts with a groove (24) formed in the shank part (16) of the dental drill (10) and thus fixes the drill stop sleeve (22) on the dental drill (10). The drill stop sleeves (22) of equal length are held in a blister of a set, the blister having, for each drill stop sleeve (22), a specific receiving recess that is closed in a sterile manner. Each blister comprises several drill stop sleeves with sleeve diameters corresponding to the bore diameters.

11 Claims, 10 Drawing Sheets

U.S. PATENT DOCUMENTS

| | | |
|---|---|---|
| 2006/0004372 A1 | 1/2006 | Zwirnmann |
| 2006/0188840 A1* | 8/2006 | Verban ........................ 433/75 |
| 2007/0099150 A1* | 5/2007 | Muller et al. ............... 433/165 |

FOREIGN PATENT DOCUMENTS

| | | | |
|---|---|---|---|
| EP | 0373111 | A2 | 6/1990 |
| EP | 035059 | A2 | 9/1990 |
| FR | 2878429 | A | 6/2006 |
| WO | WO 00/25695 | A | 5/2000 |
| WO | WO 00/74585 | A2 | 12/2000 |
| WO | WO 2006/062613 | A | 6/2006 |

* cited by examiner

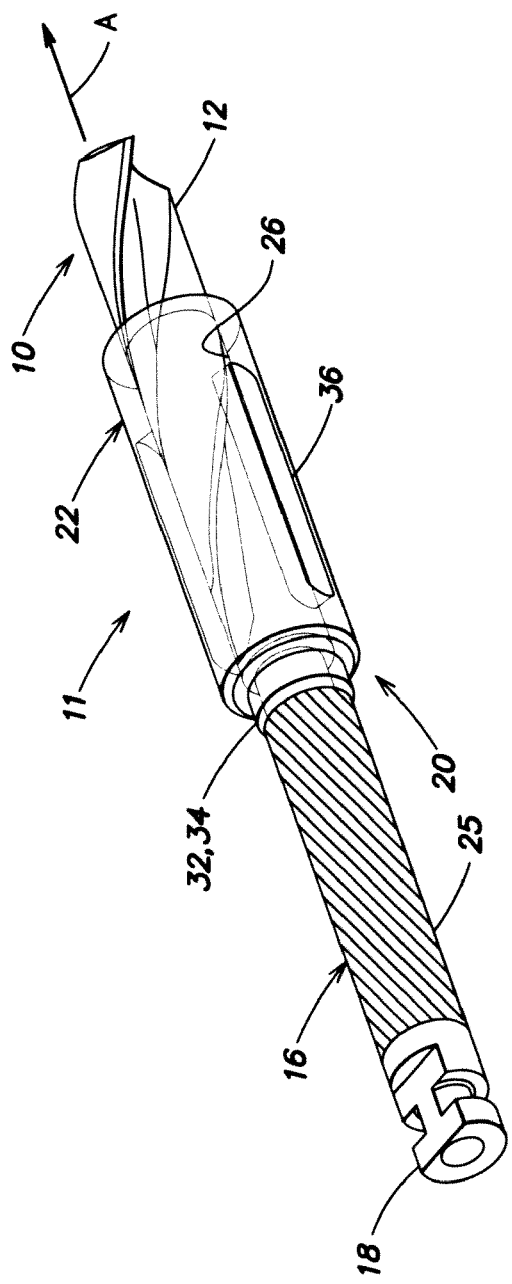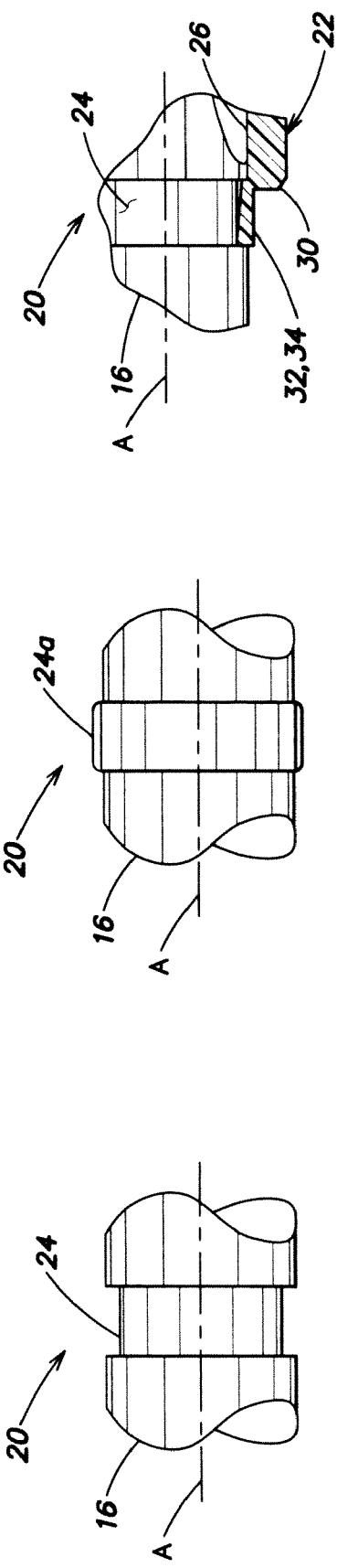
FIG. 3
FIG. 4
FIG. 4A
FIG. 5

DRILL STOP SLEEVE FOR A DENTAL DRILL, DENTAL DRILL DEVICE WITH A DRILL STOP SLEEVE, AND SET CONTAINING SEVERAL DRILL STOP SLEEVES

FIELD OF THE INVENTION

The present invention relates to a drill stop sleeve, a dental drill device, and to a set containing several drill stop sleeves.

BACKGROUND

A drill stop sleeve and a dental drill device comprising a dental drill and a drill stop sleeve are known from U.S. Pat. No. 6,514,258 B1. Said document discloses a dental drill that has a drilling end and a cylindrical shank part. At an end area of the shank part directed toward the drilling end, it is provided with a cuff-like thickened area that has a greater diameter than the bore diameter of the dental drill. At one of its end faces, the drill stop sleeve has an abutment surface and, adjoining the other end face, a clamp area intended to engage around the thickened area. In the clamp area, the drill stop sleeve has the greatest external diameter, which is formed by several resilient clamp fingers. These are formed by gaps extending in the longitudinal direction of the drill stop sleeve and open at the end. The drill stop sleeve can be pushed onto the dental drill from the direction of the drilling end, by which means the clamp area comes to engage with the thickened area in the manner of a snap-fit closure.

In order to drill a hole with a defined drilling depth, U.S. Pat. No. 6,514,258 B1 discloses drill stop sleeves of different lengths that can be fitted onto the dental drill of given length. The drilling depth of the dental drill device is in each case defined by the distance between the drilling end and the abutment surface of the fitted drill stop sleeve. Said document also discloses that dental drills with two different bore diameters can be used. As regards the material used for the drill stop sleeve, the document states that rigid, stiff materials such as metal or plastic can be used.

A disadvantage of the drill stop sleeve according to this prior art has proven to be that the view of the drilled hole is partially obstructed by the drill stop sleeve, in particular just before the abutment surface reaches the bone or the tissue or material surrounding the drilled hole. A further disadvantage has proven to be that several finger-like clamp elements are formed in the clamp area, making production complicated and therefore expensive. Another disadvantage has proven to be that the drill stop sleeve has the greatest external diameter in the clamp area, which also obstructs the view.

It would be desirable to provide a drill stop sleeve and a dental drill device that do not have the disadvantages mentioned above. Also desirable is a packaging that facilitates the handling of the drill stop sleeves.

SUMMARY OF THE INVENTION

In accordance with one embodiment, a transparent or translucent design of the drill stop sleeve means that the view of the drilled hole can be decisively improved, without having to reduce the wall thickness of the drill stop sleeve and therefore the size of the abutment surface.

According to a preferred embodiment of the drill stop sleeve, it has a radial through-opening in a hollow cylindrical area. This through-opening means that tissue and bone substance conveyed from the drilled hole can be conveyed from the radial interior of the drill stop sleeve to the outside of the drill stop sleeve. The radial through-opening also serves to ensure the cooling of the dental drill in the interior of the drill stop sleeve.

According to a preferred embodiment, the hollow cylindrical area has a greater wall thickness than the securing area, and the internal diameter of the securing area narrows in the direction of the free end. This also affords an improved view of the drilled hole.

According to a preferred embodiment of the drill stop sleeve, a means for fixing the drill stop sleeve is arranged in an end area remote from the abutment surface and is formed by a lip that is intended to interact with a holding area on the dental drill. The uninterrupted circumferential and radially elastically deformable lip ensures that the securing area of the drill stop sleeve can be made stable in a very simple way and can thus be produced inexpensively.

The dental drill device according to this embodiment permits a very simple and therefore inexpensive configuration of the dental drill and of the drill stop sleeve.

According to a preferred embodiment, the drill stop sleeve is made elastically deformable, such that it can be fitted over the shank part onto the dental drill. This elastic deformability ensures the simplest possible assembly of the drill stop sleeve onto the dental drill, without any danger of the drill stop sleeve being damaged by the cutting edges of the dental drill.

According to a preferred embodiment, the drill stop sleeve, like the dental drill, is provided with a coding, in particular a color coding. This makes it possible, for example, to very easily identify a drill stop sleeve matching the bore diameter of the dental drill.

The set according to one embodiment permits extremely simple sterile provision of the drill stop sleeves that are to be used in an operation. Before the operation, a blister containing drill stop sleeves of the desired length is selected, as a result of which, in combination with matching dental drills, the desired drilling depth is defined. In the operation, a dental drill with the smallest bore diameter is initially used together with the drill stop sleeve that matches it. If so required, the resulting drilled hole is then drilled again using the dental drill with the next biggest bore diameter, in which case the matching drill stop sleeve is again fitted onto this dental drill. If necessary, the drilling can be continued using dental drills of greater bore diameters and using the drill stop sleeves that match these.

Other particular advantages and effects are set forth in the detailed description and in the drawings.

BRIEF DESCRIPTION OF THE DRAWINGS

The invention is explained in more detail below on the basis of an illustrative embodiment depicted in the drawing in which, purely schematically:

FIG. 3 shows a perspective view of the dental drill device according to one embodiment, in which a drill stop sleeve is fitted onto the dental drill shown in FIG. 1;

FIG. 4 shows a side view of the detail indicated by "X" in FIG. 1, depicting a holding section;

FIG. 4a shows a side view similar to FIG. 4 but of an alternative embodiment having a bead (rather than a groove);

FIG. 5 shows a side view of the detail indicated by "X" in FIG. 2, depicting the holding section;

DETAILED DESCRIPTION

Figure 1:
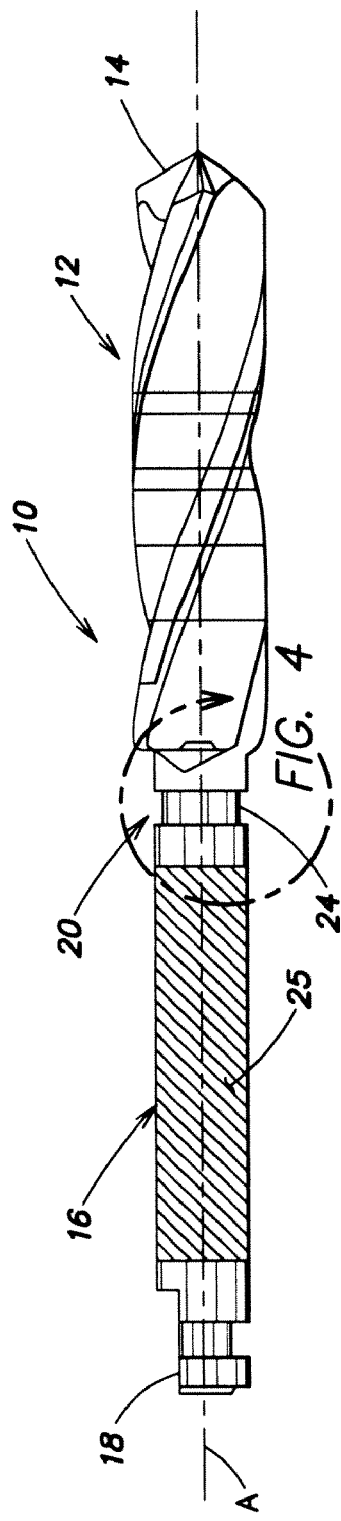
FIG. 1 shows a side view of a dental drill with a color coding on its shank part and with circular drilling depth markings on its cutting part.
Figure 2:
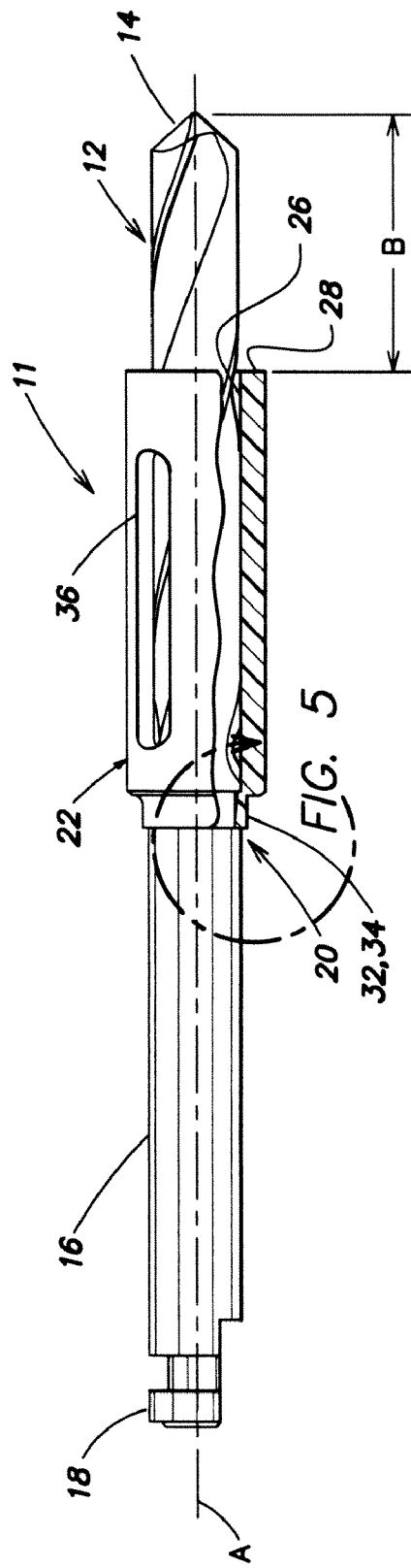
FIG. 2 shows a side view of a dental drill device according to one embodiment with a dental drill and with a drill stop sleeve fitted onto the dental drill, the drill stop sleeve being shown partially in cross section.

Two illustrative embodiments of a dental drill 10 are shown in FIGS. 1-3. The dental drill 10 comprises, on the one hand, a cutting part 12 with a drilling end 14, and, on the other hand, a shank part 16 with an exposed receiving end area 18. The receiving end area 18 is intended to be received in a generally known drill holder device and has a rotary securing means configured as a surface, and an axial securing means designed as a groove extending in the circumferential direction. The rotary securing means and the axial securing means ensure that the dental drill 10 can be brought into a fixed connection with the drill holder device, which for example is part of a drill drive or of a hand drill.

At a distance from the cutting part 12, the shank part 16 has a holding area 20 for a drill stop sleeve 22 (see FIGS. 2 and 3). As FIGS. 4 and 5 in particular show, a completely circumferential groove 24 is formed in the shank part 16 in this holding area 20. This groove 24 has two groove walls substantially at right angles to the axial direction A of the dental drill 10.

As is shown in FIGS. 1 and 3, the one illustrative embodiment of the dental drill 10 has a color coding 25 on the shank part 16, between the receiving end area 18 and the holding area 20. This color coding is formed on the dental drill by a further groove which is worked into the shank part and which is filled with a colored material. The material used is preferably ABS (acrylonitrile-butadiene-styrene copolymer). The color of the color coding indicates the bore diameter of the dental drill. Dental drills with bore diameters of 2.2 mm, 2.8 mm, 3.5 mm and 4.2 mm are preferably used. Of course, the dental drills can also have other or wider bore diameters. Dental drills with different bore diameters preferably have the same configuration of the receiving end area. Moreover, dental drills with different bore diameters have the same overall length and the same distance between the groove 24 and the drilling end.

FIGS. 2, 3 and 5-14 show the drill stop sleeves 22 that are intended to be fitted onto a dental drill 10 (see FIGS. 2, 3 and 5 in particular) in order to limit a drilling depth B. FIGS. 6-14 in particular show drill stop sleeves 22 of equal length, but which are nevertheless intended for dental drills 10 with different bore diameters.

A dental drill device is described below that is formed by a dental drill 10 with a given bore diameter and by a drill stop sleeve 22 of given length matching this dental drill 10.

To limit the drilling depth B, the drill stop sleeve 22 comprises, on the one hand, an abutment surface 28 located at the free end of a hollow cylindrical area 26. The inner circumferential surface of the hollow cylindrical area 26 is intended to bear on the cutting part 12 of the dental drill 10 and consequently has an internal diameter that corresponds substantially to the bore diameter of the dental drill 10. Therefore, this internal diameter is also referred to as the bore diameter, or as the sleeve diameter corresponding to the bore diameter. At the end remote from the abutment surface 28, the hollow cylindrical area 26 of the drill stop sleeve 22 merges into a securing area 32. In the securing area 32, the drill stop sleeve 22 has an uninterrupted circumferential lip 34 that is intended to engage in the groove 24 in the holding area 20 of the dental drill 10. A free end face of the lip 34 interacts with the groove wall directed toward the receiving end area 18. The other groove wall interacts with a radially protruding abutment surface of the lip 34. The drill stop sleeve 22 fitted onto the dental drill 10 is fixed in the axial direction A of the dental drill 10 by means of the engagement of the lip 34 in the groove 24, thereby defining the drilling depth B, which corresponds to the distance of the abutment surface 28 from the drilling end 14 of the dental drill 10.

In order to fix the drill stop sleeve 22 on the dental drill 10, it is pushed, with the abutment surface 28 to the front, onto the dental drill 10 from the direction of the receiving end area 18. In this process, the lip 34 is elastically deflected out in the radial direction or elastically stretched in the circumferential direction and, as soon as the free end of the lip 34 reaches the groove 24 when the drill stop sleeve 22 is pushed onto the dental drill 10, it snaps into said groove 24 and is consequently held in the axial direction A on the dental drill.

To ensure reliable elastic deformation of the lip 34, the drill stop sleeve 22 has a substantially smaller wall thickness in the securing area 32 than it does in the hollow cylindrical area 26. In the hollow cylindrical area 26, the wall thickness is constant. In particular, the drill stop sleeve 22 has its maximum external diameter in the hollow cylindrical area 26.

The holding area 20 can of course also have a different design. For example. instead of the groove 24, the holding area 20 can comprise a bead 24a extending in the circumferential direction (see FIG. 4a). Moreover, the lip 34 arranged in the securing area 32 of the drill stop sleeve 22 can also be formed by another means for fixing the drill stop sleeve on the dental drill. The important point is that the securing area 32 is at a distance from the abutment surface 28.

In the hollow cylindrical area 26, the drill stop sleeve 22 has two diametrically opposite radial through-openings 36, which are designed in an elongate shape in the axial direction A. These through-openings 36 are intended to ensure that material conveyed out of the drilled hole during the drilling operation can be conveyed from the interior of the drill stop sleeve 22 to the radially outer face of the drill stop sleeve 22. Moreover, the radial through-openings 36 serve to ensure the cooling of the dental drill 10 in the interior of the drill stop sleeve 22.

As is shown in FIGS. 6, 7 and 9-14, the drill stop sleeves are adapted to the abovementioned bore diameters of the dental drills 10. Corresponding to the four bore diameters of the dental drills 10, the drill stop sleeves 22 have four different sleeve diameters. The four drill stop sleeves 22 shown in the abovementioned figures are intended for different bore diameters but nevertheless have the same length, as a result of which they define the same drilling depth for different bore diameters.

The end area of the securing area 32 adjoining the hollow cylindrical area 26 is designated as intermediate area 30 and is designed slightly differently depending on the sleeve diameter of the drill stop sleeve 22. To ensure a stable transition from the lip 34 to the hollow cylindrical area 26, this intermediate area has a truncated cone design, particularly in drill stop sleeves of greater sleeve diameters.

The material used for the drill stop sleeves 22 is preferably a plastic, in particular a biocompatible plastic such as polycarbonate. For example, the product Makrolon™ from the company Bayer AG can be used. To ensure the best possible view of the drilled hole during the drilling operation, the drill stop sleeves 22 are transparent or at least translucent. In this way, throughout the entire duration of the drilling operation, in particular just before reaching and upon reaching the drilling depth defined by the dental drill device, a good view or at least an improved view of the drilled hole is guaranteed. This is not guaranteed in dental drill devices according to the prior art, because these use drill stop sleeves made of metal, for example.

Moreover, each of the drill stop sleeves 22 carries a coding, for example a color coding, which corresponds to the coding of the dental drill 10 and which indicates the internal diameter of the hollow cylindrical area 26. In this way, the user can very easily identify which drill stop sleeve 22 matches a dental drill 10 with a given bore diameter.

Moreover, the length of the drill stop sleeve 22 is indicated or suitably coded on the outer face of each drill stop sleeve 22. In addition to the length or instead of the length of the drill stop sleeve 22, the drilling depth B defined by the length of the drill stop sleeve 22 can also be indicated or coded.

Figure 15:
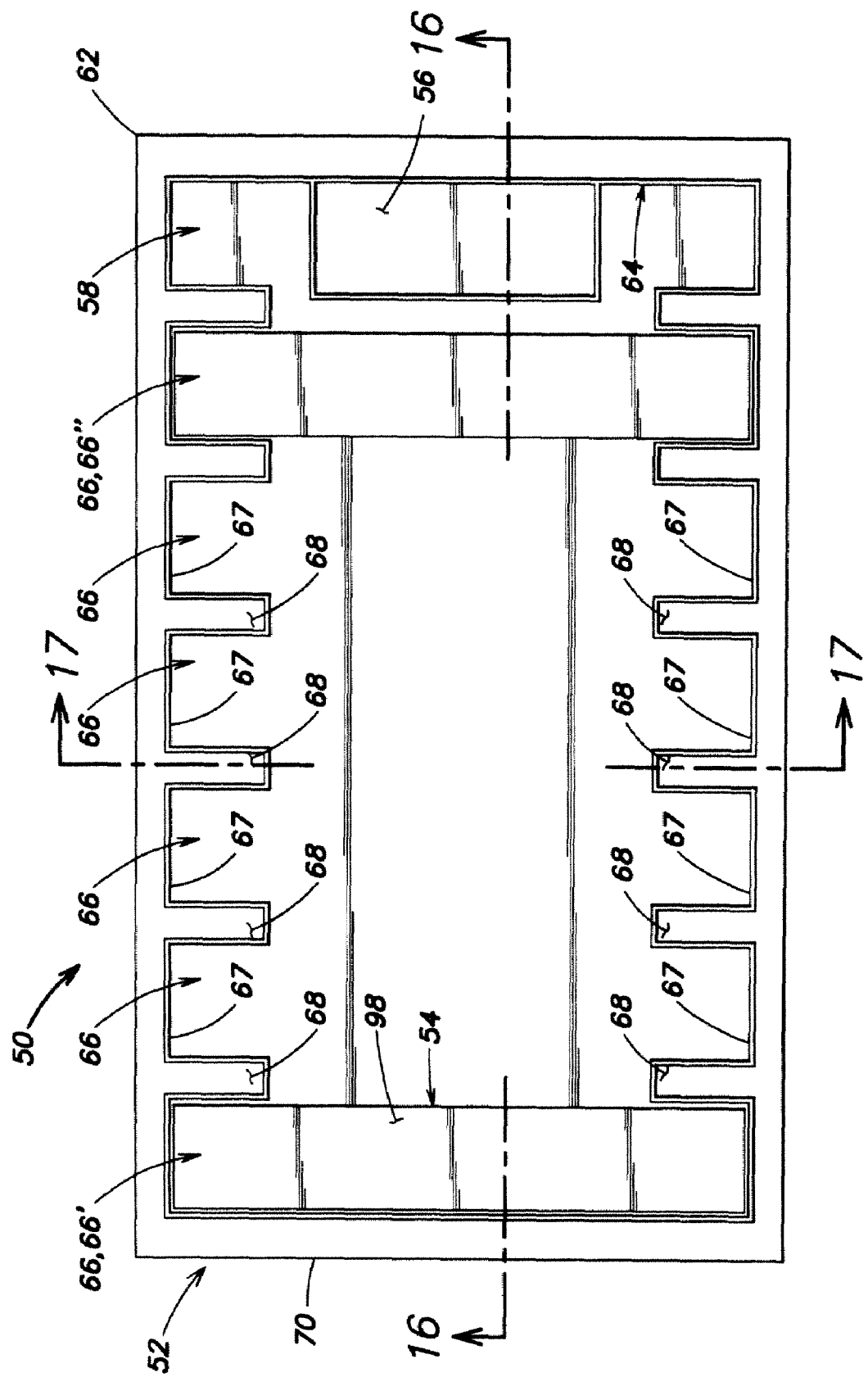
FIG. 15 shows a plan view of a set box with six holding devices for blisters and with a holding recess for an assembly aid, two of these holding devices respectively containing one blister and three blisters.
Figure 16:
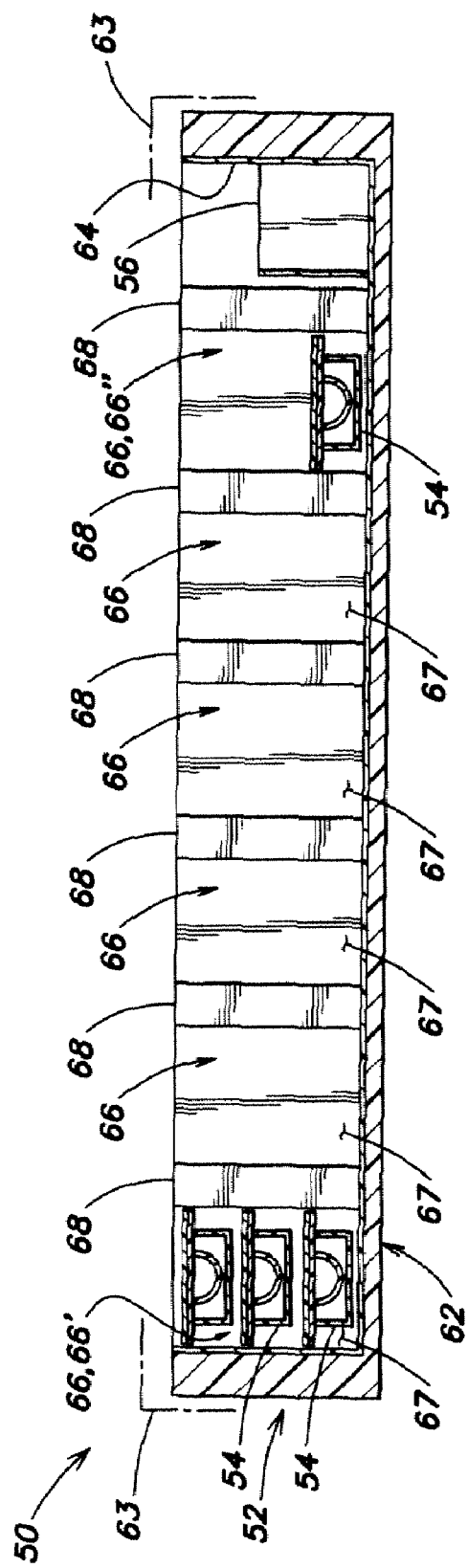
FIG. 16 shows in cross section, along the sectional plane A-A indicated in FIG. 15, the set box with the inserted blisters.
Figure 17:
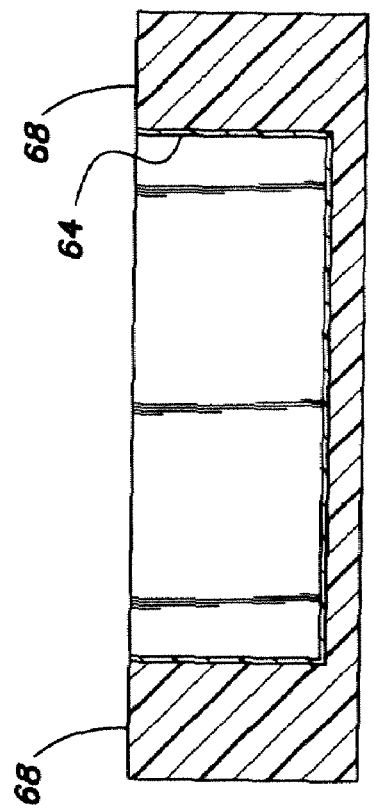
FIG. 17 shows in cross section, along the sectional plane B-B indicated in FIG. 15, the set box with the inserted blisters.
Figure 18:
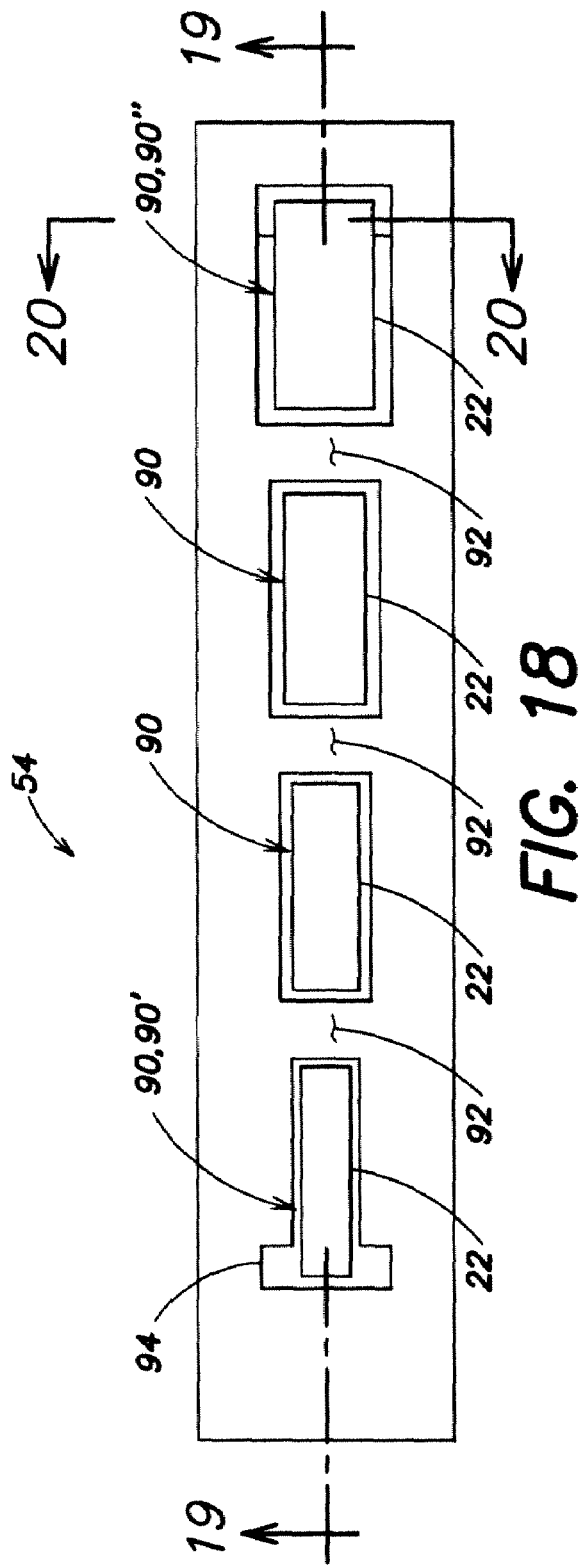
FIG. 18 shows a plan view of a blister with a total of four receiving recesses for in each case one drill stop sleeve, all the drill stop sleeves having the same length, and each of the drill stop sleeves being designed for a dental drill with a different bore diameter.
Figure 19:
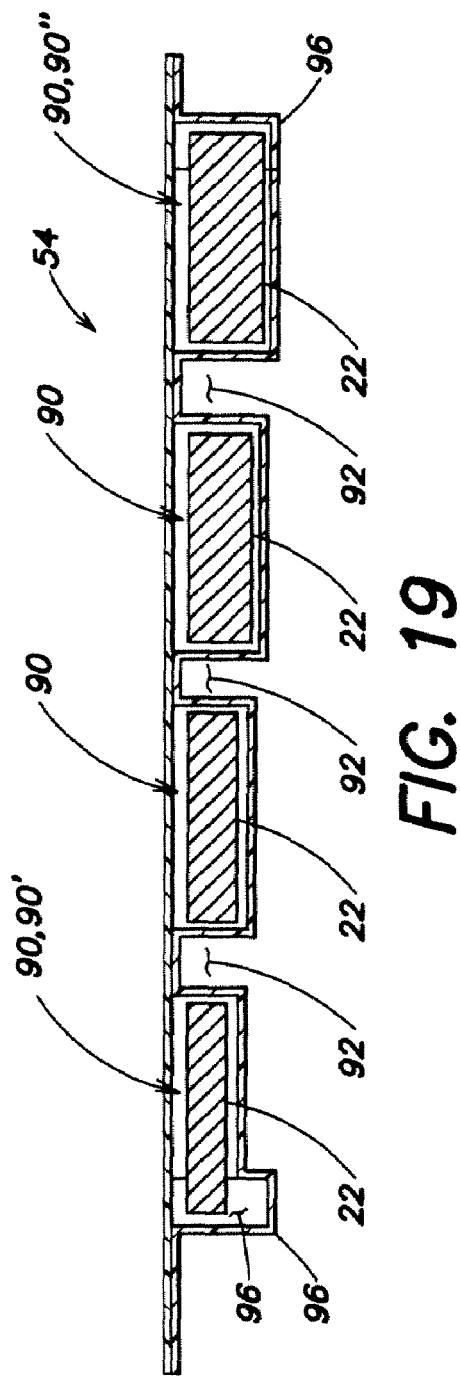
FIG. 19 shows the blister in a cross-sectional view according to the sectional plane A-A indicated in FIG. 18.
Figure 21:
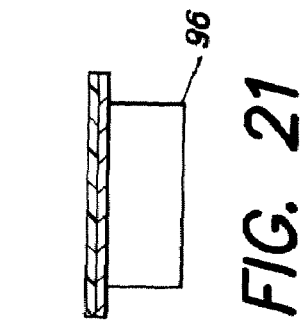
FIG. 21 shows a side view of the blister according to FIG. 18.
Figure 20:
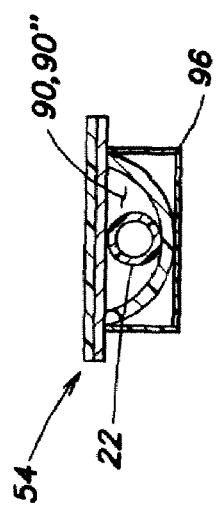
FIG. 20 shows the blister in a cross-sectional view according to the sectional plane B-B indicated in FIG. 18.

FIGS. 15-17 show a set 50 comprising several drill stop sleeves 22 of different lengths and for dental drills 10 with different bore diameters. The set 50 also comprises a set box 52 with blisters 54 arranged in it (see FIGS. 18-22). The set box 52 also comprises a receiving recess 58 for a pack insert leaflet and another one for an assembly block 56 (see in particular FIGS. 23-27). The assembly block 56 allows the drill stop sleeves 22 to be assembled on the dental drills 10 and disassembled from the dental drills 10 in the simplest possible way.

The set box 50 shown in FIGS. 15-17 comprises an outer casing 62 which forms a bottom part of the box and onto which a lid 63 (indicated by dotted lines in FIG. 16) can be fitted in a known manner. This lid 63 is preferably made of a transparent material, and the outer casing 62 is preferably made of a non-transparent material. A preferably thin-walled box insert 64 made of plastic is inserted into the outer casing 62. It serves to hold six blisters 54 alongside one another and, in each case, three blisters above one another, and also to receive the assembly block 56 and the pack insert leaflet. Of course, the box insert 64 can also be designed such that another number of blisters 54 can be arranged alongside one another and above one another.

To keep the blisters 54 in order alongside one another in the box insert 64, the box insert 64 has several integrally designed blister-receiving recesses 66, each of which can receive three blisters 54 arranged above one another. The blister-receiving recesses 66 are arranged alongside one another in such a way that their long sides lie next to one another. In the longitudinal direction of the blister-receiving recesses 66, they are delimited by side walls 67 of the box insert 64. In order also to delimit the blister-receiving recesses in their transverse direction, the side walls 67 each have a protruding step-like separating element 68 arranged between two adjacent blister-receiving recesses 66. The one outermost blister-receiving recess 66' is further delimited by a transverse wall 70 of the box insert 64 connecting the side walls 67 to one another, and the other outermost blister-receiving recess 66" is delimited by another pair of separating elements 68, which delimit this blister-receiving recess 66" from the likewise integrally formed receiving recess 58 for the pack insert leaflet.

The receiving recess for the assembly block 56 is designed integrally with the receiving recess 58 for the pack insert leaflet and, at the center, continues further down from the receiving recess 58 for the pack insert leaflet.

The blister 54 shown in FIGS. 18-22 has four receiving recesses 90, which are analogous to the four bore diameters of the dental drills 10 and are arranged one after another in the longitudinal direction of the blister 54. The receiving recesses 90 are each separated from one another by a partition wall 92. Each receiving recess 90 accommodates a drill stop sleeve 22, of which the longitudinal axis extends in the longitudinal direction of the blister 54. The blister 54 holds four drill stop sleeves 22 for the four different bore diameters, but only for one drilling depth. The four receiving recesses 90 all have the same length, but the depths and widths are adapted to the respective drill stop sleeve 22 received in the receiving recess 90, the depth in particular being adapted such that the drill stop sleeve 22 lies just underneath the upper edge of the receiving recess 90. In other words, the receiving recess 90 is slightly deeper than the external diameter of the drill stop sleeve 22 received in the receiving recess 90. The arrangement of the receiving recesses 90 is chosen such that, in the longitudinal direction of the blister 54, the drill stop sleeves 22 are arranged in order of increasing bore diameter.

Figure 22:
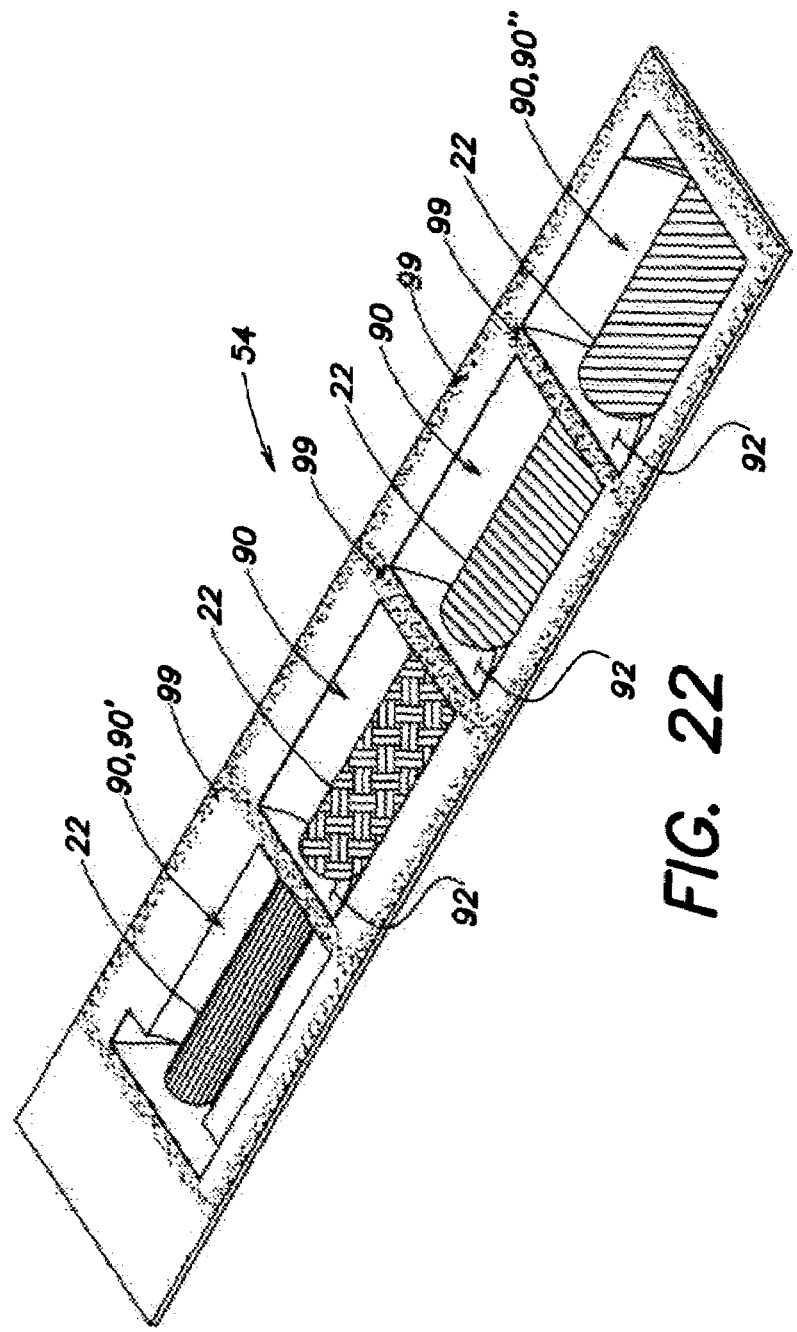
FIG. 22 shows a perspective view of the blister according to FIGS. 18-21.

It will also be clearly seen from FIG. 22 that the drill stop sleeves 22 received in the blister 54 are color-coded. They can, for example, be colored blue, yellow, red and green.

To ensure that the blisters 54 can be stacked without any problem, the receiving recess 90' for the drill stop sleeve 22 with the smallest bore diameter has a downward continuation 94, such that the maximum depth of this receiving recess is the same as the depth of the receiving recess for the drill stop sleeve with the greatest bore diameter. Moreover, this continuation 94 forms a surface 96 on the outer, downwardly directed face. By means of this surface 96, and another analogous surface 96 formed on the receiving recess 90" for the drill stop sleeve 22 with the greatest bore diameter, it is possible to ensure that, when the blister 54 is placed on a horizontal plane, the top of the blister 54 is likewise oriented horizontally.

Each receiving recess 90 is closed in a sterile manner by means of a tear-off strip 98 (see FIG. 15) that extends along the full length of the blister. For this purpose, each receiving recess 90 is surrounded by a sealing seam area 99 (see FIG. 22), which encloses the receiving recess 90 and in which the tear-off strip 98 is sealed fixedly to the blister 54. A sterile packaging of each individual drill stop sleeve 22 can be easily achieved in this way.

Figure 23:
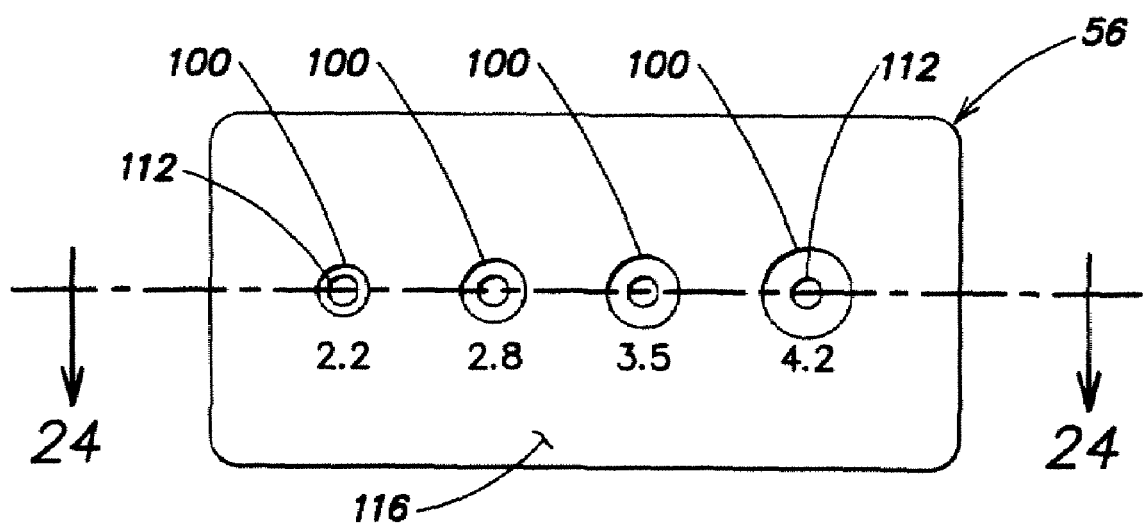
FIG. 23 shows a plan view of the assembly block for assembly and disassembly of the drill stop sleeves on the dental drill, where, for assembly purposes, the assembly block comprises, for each bore diameter of the dental drills, a bore that is slightly greater than the bore diameter of the corresponding dental drill.
Figure 24:
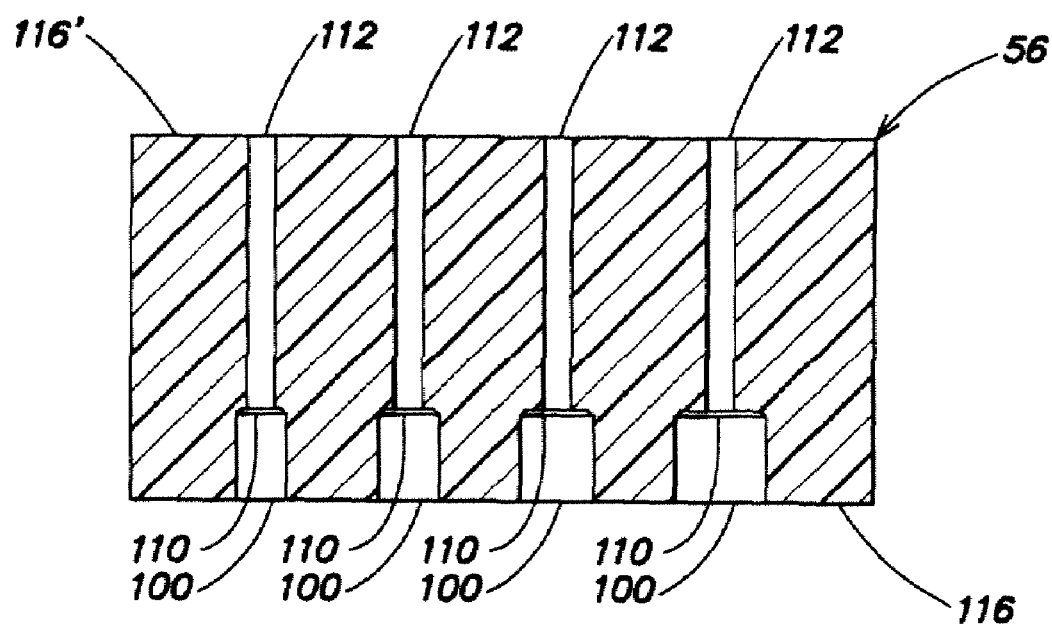
FIG. 24 shows a cross-sectional view of the assembly block according to the sectional plane A-A indicated in FIG. 23.
Figure 25:
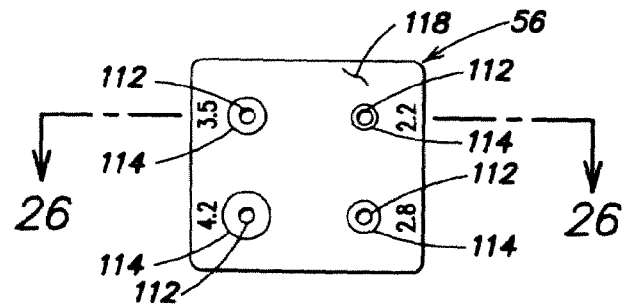
FIG. 25 shows a side view of the assembly block according to FIGS. 23 and 24, this view showing the bores for disassembly of the drill stop sleeves from the dental drills.
Figure 26:
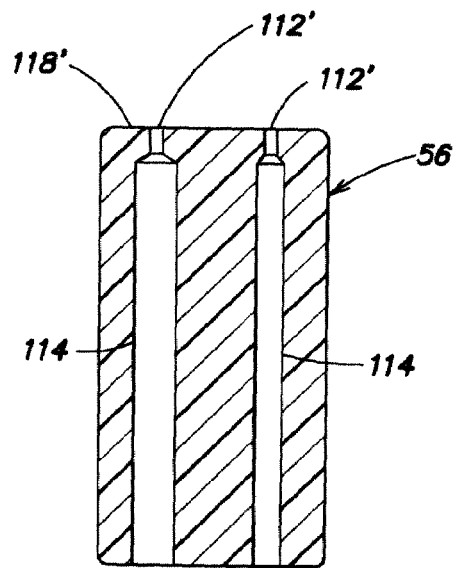
FIG. 26 shows a cross-sectional view of the assembly block according to the sectional plane B-B indicated in FIG. 24.
Figure 27:
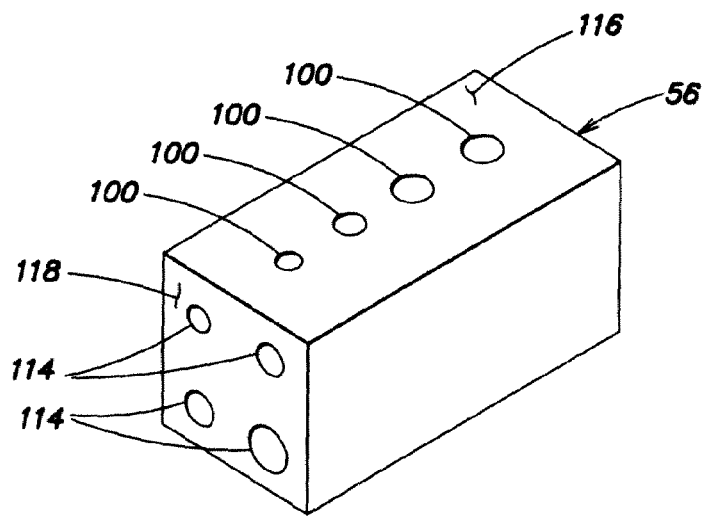
FIG. 27 shows a perspective view of the assembly block.

The cuboid assembly block 56 shown in FIGS. 23-27 is intended for assembly of the drill stop sleeves 22 onto the dental drills 10 and for disassembly of the drill stop sleeves 22 from the dental drills 10, and it has four longitudinal side faces 116 and two end faces 118. For assembly purposes, the assembly block 56 has, for each of the four bore diameters of the dental drills 10, an assembly recess 100 which leads from one of the longitudinal side faces 116 into the assembly block 56 and whose diameter is slightly greater than the bore diameter of the respective dental drill 10. Each of the assembly recesses 100 is limited at one end by a base 110, which forms a limit stop for a dental drill inserted into the assembly recess 100. The depth of the assembly recess 100 defined by the base 110 is chosen such that it is smaller than the minimum drilling depth defined by the longest drill stop sleeve. As is shown in FIGS. 23 and 27, the four assembly recesses 100 are arranged along a center line. Moreover, each assembly recess 100 has a through-hole 112 which extends in the axial direction of the assembly recess 100 and which facilitates the cleaning of the assembly recesses 100. The diameter of the through-hole 112 is chosen smaller than the smallest bore diameter. At one end, this through-hole 112 opens out centrally in the base 110 and, at the other end, it opens out in the opposite longitudinal side face 116' (see FIG. 24).

For disassembly purposes, the assembly block 56 has four disassembly recesses 114, which are arranged in such a way that the disassembly recesses 114 do not coincide with the assembly recesses 100. The disassembly recesses 114 lead from one of the two end faces 118 into the assembly block. The disassembly recesses 114 have a design substantially analogous to the assembly recesses 100, but have a depth that is greater than the maximum drilling depth defined by the shortest drill stop sleeve 22. From the base 110 of each disassembly recess 114, a through-hole 112' extends in the axial direction of the disassembly recess 114 to the end face 118' remote from the opening of the disassembly recess 114.

The drill stop sleeve 22, the dental drill device 11 and the set 50 are used as follows:

For example, in order to drill a hole with a predetermined depth and a predetermined diameter in the jaw of a patient, a hole with the desired length, but with a smaller bore diameter is first drilled by means of one dental drill 10. Thereafter, this drilled hole is then extended to the desired diameter in one or more steps using dental drills 10 of greater bore diameters.

To ensure that the drilled hole will have the desired depth, the drilling depth of the dental drill is limited by using a drill stop sleeve of appropriate length. Since drill stop sleeves 22 of equal lengths for the different bore diameters are stored in the same blister 54, the blister 54 containing the drill stop sleeves 22 of the desired length are removed from the set box 50 before the operation. Since a blister 54 only contains drill stop sleeves 22 of equal length, an inadvertent mix-up of drill stop sleeves 22 of different lengths is ruled out. Consequently, the set and the dental drill device 11 can, for example, reliably avoid injury to the nerves of the jaw.

Thereafter, the appropriate drill stop sleeves 22 are fitted onto the dental drills 10 with the desired bore diameters, the coding clearly indicating which drill stop sleeve 22 is to be fitted onto which dental drill 10.

To fit the drill stop sleeves 22 onto the dental drills 10, the latter are introduced, with the drilling end 14 first, into the corresponding assembly recesses 100 of the assembly block 56, as a result of which, on the one hand, the sharp and sensitive cutting part 12 is protected from damage during assembly and, on the other hand, the risk of injury to the person carrying out the assembly is reduced. Thereafter, the corresponding drill stop sleeves 22 are pushed, with the abutment surface 28 to the front, onto the dental drills 10 from the direction of the receiving end area 18, until the lip 34 of each drill stop sleeve 22 snaps into the groove 24 on the shank part 16 of the corresponding dental drill 10.

If a drill stop sleeve 22 is to be removed from the dental drill 10 after the hole has been drilled, for example because the dental drill is to be used for another drilled hole with a different length, the dental drill 10 is introduced, with the drilling end 14 first, into the appropriate disassembly recess 114 of the assembly block 56, until the abutment surface 28 of the drill stop sleeve 22 touches the assembly block 56. By then pressing the dental drill 10 into the disassembly recess 114, the engagement of the lip 34 of the drill stop sleeve 22 in the groove 24 of the dental drill 10 is released, and the drill stop sleeve 22 can be removed from the dental drill 10. Once again, by using the assembly block 56 for disassembly of the drill stop sleeve 22, damage to the dental drill 10 can be avoided, and the risk of injury to the person carrying out the disassembly work can be reduced.

Figure 28:
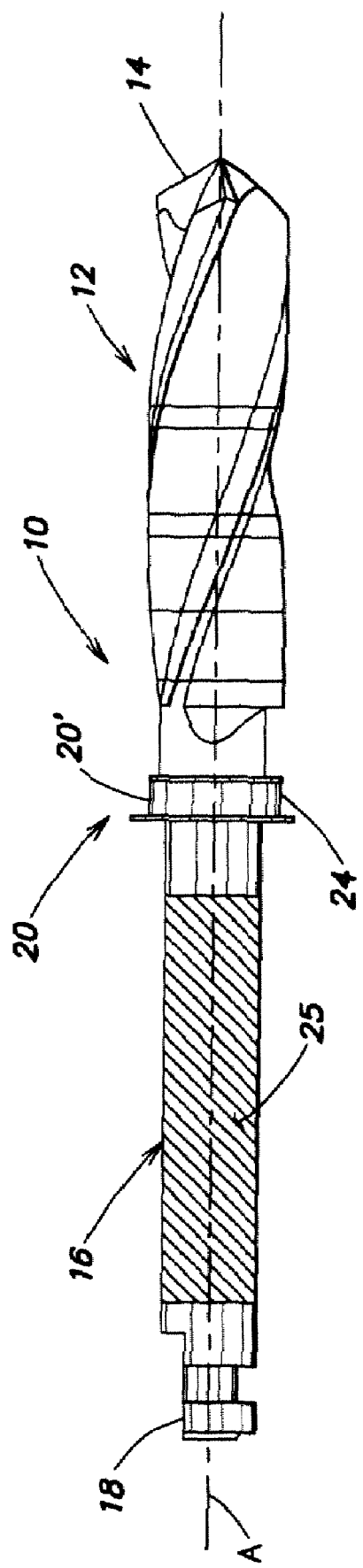
FIG. 28 shows a side view of a further embodiment of a dental drill which, compared to the dental drill shown in FIG. 1, has a radial thickening in which a groove is formed for securing the drill stop sleeve on the dental drill.

Another embodiment of the dental drill 10 is shown in FIG. 28. In contrast to the dental drills 10 shown in FIGS. 1 to 3, this dental drill has a radial thickening 20' of the shank part 16 in the holding area 20, into which a groove 24 is worked. The two groove walls are formed by circle sections in the holding area 20, the circle section directed toward the receiving end area 18 having a greater diameter than the section directed toward the drilling end 14. The circle section directed toward the drilling end 14 has a diameter that is substantially identical to the bore diameter of the cutting part 12.

Figure 8:
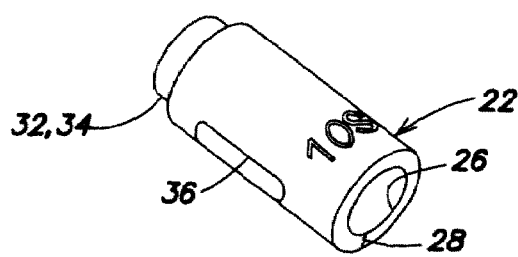
FIG. 8 shows a perspective view of the drill stop sleeve according to FIG. 6.
Figure 6:
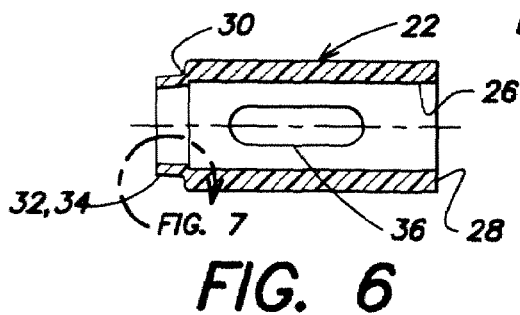
FIG. 6 shows a cross-sectional view of a first embodiment of the drill stop sleeve.
Figure 7:
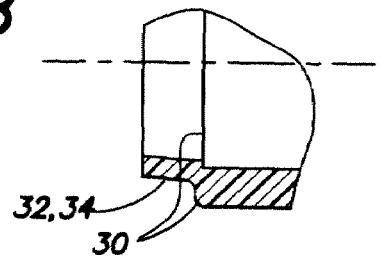
FIG. 7 shows a cross-sectional view of the detail indicated by "X" in FIG. 6.
Figure 9:
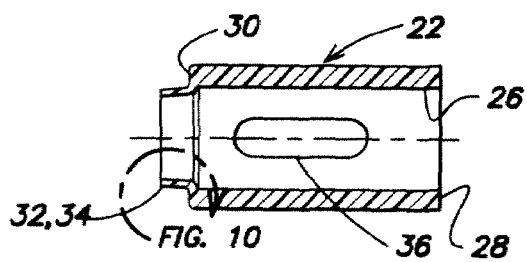
FIG. 9 shows a cross-sectional view of an embodiment of the drill stop sleeve which, compared to the drill stop sleeve shown in FIGS. 6 to 8, is for a dental drill with a greater bore diameter but having the same length.
Figure 10:
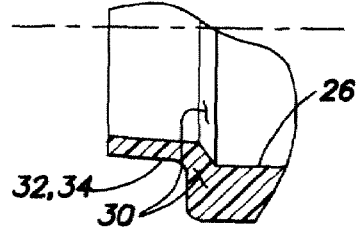
FIG. 10 shows a cross-sectional view of the detail indicated by "X" in FIG. 9.
Figure 11:
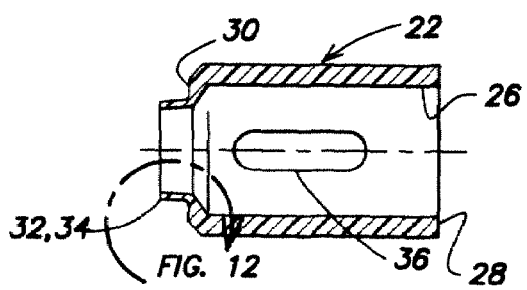
FIG. 11 shows a cross-sectional view of an embodiment of the drill stop sleeve which, compared to the drill stop sleeve shown in FIGS. 9 and 10, is for a dental drill with a greater bore diameter but having the same length.
Figure 12:
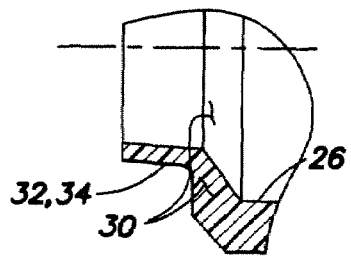
FIG. 12 shows a cross-sectional view of the detail indicated by "X" in FIG. 11.
Figure 13:
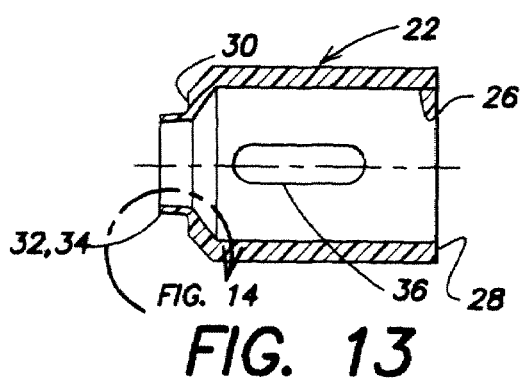
FIG. 13 shows a cross-sectional view of an embodiment of the drill stop sleeve which, compared to the drill stop sleeve shown in FIGS. 11 and 12, is for a dental drill with a still greater bore diameter but having the same length.
Figure 14:
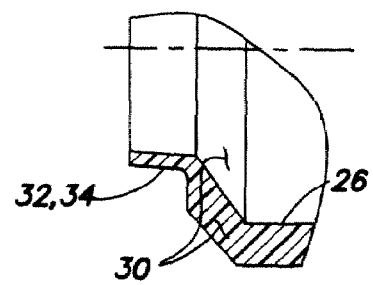
FIG. 14 shows a cross-sectional view of the detail indicated by "X" in FIG. 13.

A drill stop sleeve matching the dental drill 10 shown in FIG. 28 has basically the same shape and properties as the drill stop sleeve 22 described in connection with FIGS. 6 to 8, but is pushed with the securing area 32 first onto the dental drill 10, from the direction of the drilling end 14. The lip 34 of the drill stop sleeve 22 is once again intended to engage in the groove 24 in the holding area 20.

Another embodiment of the drill stop sleeve can be substantially cylindrical along its entire length. In the securing area, such a drill stop sleeve has a complete circumferential radial groove which is worked into its radially inward jacket surface and which interacts with the circle section directed toward the drilling end 14, in order to secure the drill stop sleeve on the dental drill 10. The circle section directed toward the receiving end area 18 interacts, as a limit stop, with an end face of the securing area of the drill stop sleeve.

The securing area of a drill stop sleeve intended for the dental drill according to FIG. 28 is again elastically deformable. For other properties and materials, reference is made to the drill stop sleeves described above in connection with FIGS. 6 to 8.

The above-described dental drills 10 and drill stop sleeves 22 can be designed to be used only for a single operation. Since it is therefore possible to dispense with sterilization after use of the dental drills 10 and drill stop sleeves 22, materials, in particular plastics, can be used that are difficult to sterilize and are inexpensive compared to sterilizable plastics.

The invention claimed is:

1. A set comprising:
several drill stop sleeves designed to be fitted onto dental drills of different bore diameters and which have different lengths and different sleeve diameters corresponding to the bore diameters;
the drill stop sleeves being held in blisters that have a separate receiving recess for each drill stop sleeve, each blister comprising several drill stop sleeves of equal length and a drill stop sleeve of each sleeve diameter;
an assembly block for assembly and disassembly of the drill stop sleeves onto and from the dental drills, respectively;
the assembly block having, for dental drills of each bore diameter, a circular cylindrical assembly recess with a slightly greater diameter than the bore diameter and limited at one end by a base that forms a limit stop for the dental drill, the depth of the assembly recess being smaller than a minimum drilling depth, the minimum drilling depth being defined by a distance of an abutment surface of the longest drill stop sleeve mounted on the dental drill from a drill end of the dental drill; and
the assembly block having, for dental drills of each bore diameter, a circular cylindrical disassembly recess with a slightly greater diameter than the bore diameter and whose depth is greater than a maximum drilling depth, the maximum drilling depth being defined by a distance of an abutment surface of the shortest drill stop sleeve mounted on the dental drill from the drill end of the dental drill.

2. The set as claimed in claim 1, including:
a set box;
wherein blisters containing drill stop sleeves of different lengths are arranged next to one another; and
blisters containing drill stop sleeves of equal lengths are arranged above one another in the set box.

3. The set as claimed in claim 1, wherein:
at least one drill stop sleeve is made of plastic and can be fitted onto one of the dental drills, the at least one drill stop sleeve having a hollow cylindrical area and the abutment surface of the at least one drill stop sleeve being at a free end of the hollow cylindrical area;
the at least one drill stop sleeve having a securing area at a distance from the abutment surface, the securing area having a means for fixing the drill stop sleeve on the dental drill; and
wherein the at least one drill stop sleeve is transparent or translucent.

4. The set as claimed in claim 3, wherein:
the securing area is arranged at the end of the at least one drill stop sleeve remote from the abutment surface.

5. The set as claimed in claim 3, wherein:
the at least one drill stop sleeve having a radial through-opening in the hollow cylindrical area in the middle of the drill stop sleeve in a longitudinal direction.

6. The set as claimed in claim 3, wherein:
the hollow cylindrical area is designed to bear radially on an outside of a cutting part of the dental drill, and has a greater wall thickness than the securing area; and
the securing area has an internal diameter that narrows in the direction of the free end.

7. The set as claimed in claim 3, comprising:
at least one dental drill having a cutting part with a drilling end and a shank part with a receiving end area, designed to be received in a drill-holder device;
a groove is formed on the shank part or a bead is formed in a holding area, which interacts with the securing area of the drill stop sleeve such that a drilling depth (B) is defined by the distance from the drilling end to the abutment surface of the drill stop sleeve; and
the drill stop sleeve, in the securing area, has an uninterrupted circumferential lip that interacts with the groove or bead, respectively.

8. The set as claimed in claim 7, wherein:
the shank part has the holding area for the drill stop sleeve; and
a completely circumferential groove is worked into the shank part, into which the circumferential lip engages.

9. The set as claimed in claim 7, wherein:
the circumferential lip is elastically deformable such that the drill stop sleeve can be fitted over the shank part onto the dental drill.

10. The set as claimed in claim 7, wherein:
the drill stop sleeve and the dental drill have a coding for identifying the internal diameter of the hollow cylindrical area and the bore diameter of the dental drill, respectively.

11. The set as claimed in claim 10, wherein the coding is a color coding.

* * * * *